US010881785B2

(12) United States Patent
Ambrosina et al.

(10) Patent No.: US 10,881,785 B2
(45) Date of Patent: Jan. 5, 2021

(54) FLUID PUMP ASSEMBLY AND LOADING OF SAME INTO A FLUID DELIVERY SYSTEM

(71) Applicant: Ivenix, Inc., Amesbury, MA (US)

(72) Inventors: Jesse E. Ambrosina, Topsfield, MA (US); Benjamin G. Powers, Portsmouth, NH (US)

(73) Assignee: Ivenix, Inc., North Andover, MA (US)

( * ) Notice: Subject to any disclaimer, the term of this patent is extended or adjusted under 35 U.S.C. 154(b) by 216 days.

(21) Appl. No.: 15/852,461

(22) Filed: Dec. 22, 2017

(65) Prior Publication Data

US 2018/0147342 A1    May 31, 2018

Related U.S. Application Data

(63) Continuation of application No. 14/608,556, filed on Jan. 29, 2015, now Pat. No. 9,849,231.

(51) Int. Cl.
*A61M 5/142*   (2006.01)
*A61M 5/168*   (2006.01)
(Continued)

(52) U.S. Cl.
CPC ...... *A61M 5/14224* (2013.01); *A61M 5/1407* (2013.01); *A61M 5/16827* (2013.01);
(Continued)

(58) Field of Classification Search
CPC .... A61M 5/142; A61M 5/145; A61M 5/1452; A61M 5/14546; A61M 5/1456;
(Continued)

(56) References Cited

U.S. PATENT DOCUMENTS 5,673,588 A  * 10/1997 Raymond ............. A61M 5/142
                                                        200/400
6,231,320 B1    5/2001 Lawless et al.
(Continued)

FOREIGN PATENT DOCUMENTS

WO    WO 2014 043499       3/2014

OTHER PUBLICATIONS

Notification and Transmittal of the International Search Report and the Written Opinion of the International Searching Authority for PCT/US2016/012162, dated Apr. 21, 2016.
(Continued)

*Primary Examiner* — Bhisma Mehta
*Assistant Examiner* — James D Ponton
(74) *Attorney, Agent, or Firm* — Armis IP Law, LLC

(57) ABSTRACT

A fluid delivery system comprises: a control interface and multiple unique loading guides. The control interface of the fluid delivery system is configured to accept a fluid pump assembly. The multiple loading guides are retractable from the fluid delivery system to retain and control movement of a facing of the fluid pump assembly to contact the control interface on the facing of the fluid delivery system. In one configuration, the control interface is disposed in a cavity of the fluid delivery system; the multiple loading guides are disposed at locations in proximity to the cavity. The multiple loading guides can be configured to slidably retract in unison to support substantially orthogonal insertion of the fluid pump assembly into the cavity of the fluid delivery system.

18 Claims, 14 Drawing Sheets

(51) Int. Cl.
*A61M 5/14* (2006.01)
*A61M 5/145* (2006.01)
*A61M 5/38* (2006.01)

(52) U.S. Cl.
CPC .......... *A61M 5/16854* (2013.01); *A61M 5/38* (2013.01); *A61M 2005/14268* (2013.01); *A61M 2005/14573* (2013.01); *A61M 2205/121* (2013.01)

(58) Field of Classification Search
CPC .............. A61M 5/14566; A61M 5/172; A61M 5/14224; A61M 5/16827; A61M 5/16854; A61M 2005/14208; A61M 2005/14573; A61M 2005/14268; A61M 2205/12; A61M 2205/121
See application file for complete search history.

(56) References Cited

U.S. PATENT DOCUMENTS

| | | |
|---|---|---|
| 7,258,534 B2 | 8/2007 | Fathallah et al. |
| 2003/0214412 A1 | 11/2003 | Ho et al. |
| 2005/0063831 A1* | 3/2005 | Fathallah .......... A61M 5/14224 417/63 |
| 2012/0209169 A1 | 8/2012 | Morris et al. |
| 2013/0071272 A1 | 3/2013 | Juretich et al. |
| 2014/0135731 A1 | 5/2014 | Breitweiser et al. |
| 2016/0151560 A1 | 6/2016 | Toro et al. |

OTHER PUBLICATIONS

Supplementary European Search Report for EP 16 74 3820, dated Jan. 16, 2018.

* cited by examiner

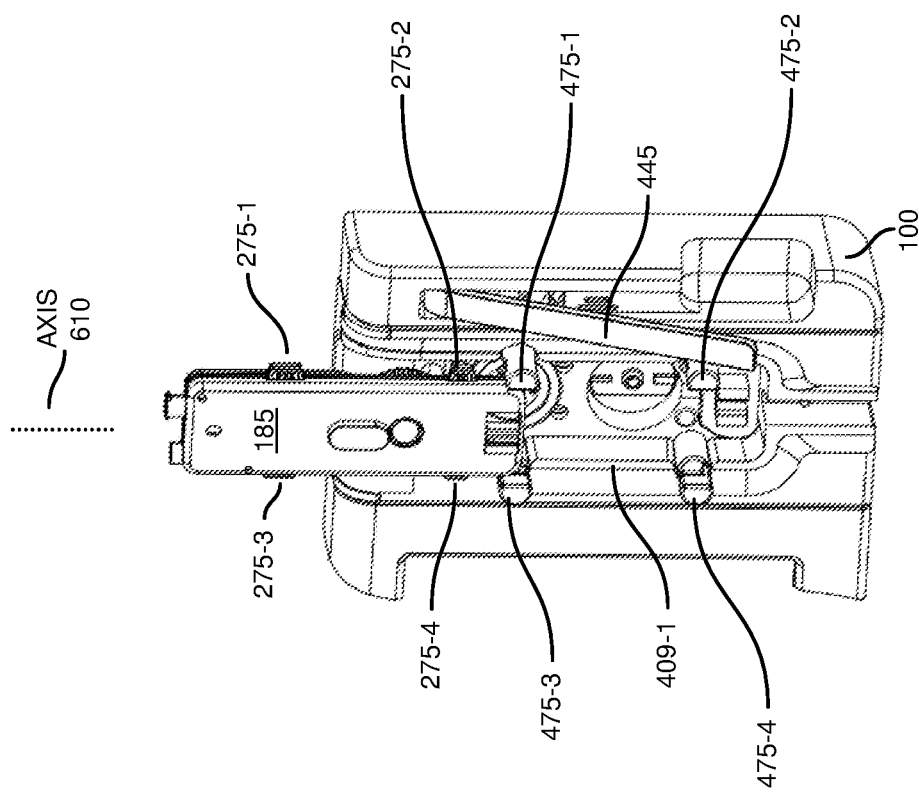

FLUID PUMP ASSEMBLY AND LOADING OF SAME INTO A FLUID DELIVERY SYSTEM

RELATED APPLICATIONS

This application is a continuation of earlier filed U.S. patent application Ser. No. 14/608,556 entitled "FLUID PUMP ASSEMBLY AND LOADING OF SAME INTO A FLUID DELIVERY SYSTEM," filed on Jan. 29, 2015, the entire teachings of which are incorporated herein by this reference.

BACKGROUND

In accordance with conventional fluid handling devices, particularly infusion pumps, it is often required for a respective caregiver to manually insert a disposable infusion tube set into a fluid delivery system for delivery of fluid to a patient. In certain instances, when operating a pumping mechanism that utilizes a rotational or linear peristaltic pump mechanism, the user must "thread" the tubing into the mechanical drive elements. It may be further required that one or more ultrasonic bubble detectors and/or pressure sensors align properly before the pump can be used.

Thus, in general, setting up a conventional fluid delivery system for use is a time-consuming and error-prone process. Improper setup may also result in certain important safety features being disabled. If the pump is not set up correctly before use, the pump may malfunction, causing possible injury or death.

Certain conventional fluid handling devices include a safety feature such as "anti-free flow" prevention mechanisms. In general, an anti-free flow mechanism includes a physical clamp that clamps off a flow of fluid to a patient if the tube set is removed from the pump. Because they are prone to failure, these conventional mechanically actuated clamps have been common sources of recalls.

In accordance with both straight tube and cassette-based conventional designs, it is common to utilize a door or some other mechanism to fully envelope the disposable cassette into a respective housing. This impedes the caregiver from being able to view, inspect, and observe the system for proper operation. If something were to get caught in the door, such as another tube or piece of clothing while the door is being locked closed, the user typically would not be able to easily see the obstruction. This can lead to an unsafe operating condition.

In certain instances, the process for loading a disposable cassette into a pump has greatly improved with the introduction of conventional cassette-based disposable tubing sets. With the newer conventional designs, a small custom component is added to the tubing set to provide an easier method for loading the disposable tubing set into the pump. However, certain currently available devices require careful alignment of the cassette to the pump features. This can add new complications and safety hazards.

Many cassette based fluid delivery systems require that the user slide a respective cassette into a cavity. Subsequent to insertion, a respective lever can be used to lock the cassette into place. In these cases, the tube set is obstructed from view, making it difficult to remedy a jam or failure. This can lead to delays in delivery of fluid to a respective patient.

In accordance with use of other conventional cassette-based loading designs, it is required that the mechanical interfaces to the pump are engaged manually. In other words, the force necessary to engage the pump must be completely provided by the user handling the cassette. This can be problematic for a number of reasons. For example, conventional infusion pumps are often mounted on poles with wheels. Therefore, it requires the user to use two hands to load the set: one hand to stabilize the pump/pole and the other hand to engage the set. Another problem with conventional confusion pumps is that it can be difficult to properly align the cassette to the pump. Improper alignment can lead to frustration, errors or the misleading of the set, which can lead to unsafe operation.

BRIEF DESCRIPTION OF EMBODIMENTS

In contrast to conventional techniques, embodiments herein include a fluid delivery system comprising: a control interface and multiple unique loading guides. In one embodiment, the control interface is disposed in a cavity of the fluid delivery system. The control interface of the fluid delivery system is configured to accept a fluid pump assembly. The multiple loading guides are retractable from the fluid delivery system to retain and control movement of a facing of the fluid pump assembly to contact the control interface on the facing of the fluid delivery system. Subsequent to contacting the fluid pump assembly to the control interface of the fluid delivery system, the fluid delivery system is able to control a flow of fluid associated with the fluid pump assembly.

As mentioned, in one embodiment, the control interface is disposed in a cavity of the fluid delivery system. The multiple loading guides can be disposed at locations in proximity to the cavity, facilitating insertion of the fluid pump assembly into the cavity and mating of an interface of the fluid pump assembly to the control interface of the fluid delivery system.

In accordance with more specific embodiments, the fluid pump assembly can be configured to include multiple tabs. The multiple tabs facilitate insertion of the fluid pump assembly into the cavity. For example, the multiple tabs can be configured to slide (such as in a direction along a first axis) into respective channels disposed in the loading guides. As the loading guides retract (such as in a direction along a second axis) into the fluid delivery system, they apply a respective force to the multiple tabs resulting in insertion of the fluid pump assembly into the cavity.

In one embodiment, the placement of the tabs of the fluid pump assembly into respective channels of the loading guides aligns the fluid pump assembly (such as a disposable cassette) for proper contact of the fluid pump assembly to the control interface of the fluid delivery system. As previously discussed, the control interface can be disposed in a cavity of the fluid delivery system.

In yet further more specific embodiments, each of the loading guides can be configured to include a respective channel to retain a corresponding tab disposed on the fluid pump assembly. Any of one or more of the channels in the loading guides can include a respective stop (channel block) that prevents further sliding of a tab in the corresponding channel or out of the channel. In one embodiment, the respective stop matably aligns a pneumatic port on the fluid pump assembly to a corresponding pneumatic control port in a control interface of the fluid delivery system.

By further way of example embodiment, during the fluid pump assembly insertion process, the multiple loading guides can be configured to slidably retract in unison to support substantially orthogonal insertion of the fluid pump assembly to the control interface of the fluid delivery system.

Yet further embodiments herein include fabricating all or a portion of the fluid pump assembly and its respective components using transparent material, enabling a respective caregiver to view through the fluid pump assembly into a cavity of the fluid delivery system. Prior to insertion, respective spacings between the multiple loading guides (and tabs) provide a substantially unobstructed view of inserting the fluid pump assembly into the cavity.

The fluid delivery system can include any suitable resource (such as a motor, user-controlled manual lever resource, etc.) to control movement of the multiple loading guides. In one embodiment, the fluid delivery system includes a user-controlled lever resource (manual lever) in mechanical communication with the multiple loading guides. Movement of the lever resource controls movement of the multiple loading guides. More specifically, in one embodiment, movement of the lever resource controls the retractable movement of the multiple loading guides and insertion and extraction (possibly in an orthogonal or near orthogonal manner) of the fluid pump assembly with respect to the cavity and corresponding control interface in the fluid delivery system.

In accordance with further embodiments, the user-controlled lever resource rotates about an axis and/or pivot. A force translator mechanism in the fluid delivery system receives a force produced based on the rotational movement of the user-controlled lever resource with respect to the axis and/or pivot. The translator mechanism converts the force received from the rotational movement of the user-controlled lever resource into substantially orthogonal motion of the loading guides with respect to the control interface, retracting the disposable cassette into or ejecting the disposable cassette out of a respective cavity of the fluid delivery system depending upon which way the lever resource is moved.

In accordance with still further embodiments, the fluid delivery system can include one or more spring resources disposed between the lever resource and the loading guides. The one or more spring resources facilitate conveyance of the received force (from the rotational motion) to the loading guides. In one embodiment, the one or more spring resources pulls or pushes the loading guides with a fixed force (based on the rotational motion), reducing the need for tight interface tolerances between the fluid pump assembly and the control interface of the fluid delivery system.

Accordingly, embodiments herein provide an improved system, method, etc., of fast and error-free loading a disposable cassette into a cavity of a fluid delivery system. In one embodiment, as generally mentioned, the cassette (fluid pump assembly) is visible during all or a portion of the insertion/extraction process including after the fluid pump assembly is completely mated to the pump mechanism in the cavity. Further, as previously discussed, a unique disposable cassette can be configured to include one or more loading tabs, which engage with specially designed retractable loading pins in the pump. In one embodiment, tab and pin arrangements can be configured in a manner such that the user of the fluid delivery system can insert the fluid pump assembly into the cavity of the fluid delivery system without substantial resistance. Use of retractable pins/guides enables a respective user to view whether the fluid pump assembly (such as including a cassette) seats properly within the cavity.

In accordance with further embodiments, as mentioned, the frame of the fluid pump assembly can be made of transparent material to further enhance the ability to view whether the fluid pump assembly seats correctly in the cavity. The mechanism utilizes a lever providing mechanical advantage. When the user applies a force to the lever, the loading guides (or pin resources) retract, pulling the cassette towards the face of the pump. In one embodiment, during this action of pulling the cassette towards the facing of the pump (such as into a respective cavity of the fluid delivery system), all necessary mechanical drive and sensor interfaces are automatically aligned and mated. Thus, the user does not need to be concerned with alignment of any of the components after the initial placement of the cassette into the loading pins. In one embodiment, subsequent to loading, the cassette (fluid pump assembly) is completely visible and any problems can easily be observed and corrected.

These and other more specific embodiments are disclosed in more detail below.

As discussed herein, techniques herein are well suited for insertion of a disposable fluid pump assembly (such as a cassette) into a cavity of a fluid delivery system that controls operation of a pump disposed in the fluid pump assembly. However, it should be noted that embodiments herein are not limited to use in such applications and that the techniques discussed herein are well suited for other applications as well.

Additionally, note that although each of the different features, techniques, configurations, etc., herein may be discussed in different places of this disclosure, it is intended, where suitable, that each of the concepts optionally can be executed independently of each other or in combination with each other. Accordingly, the one or more present inventions as described herein can be embodied and viewed in many different ways.

Also, note that this preliminary discussion of embodiments herein purposefully does not specify every embodiment and/or incrementally novel aspect of the present disclosure or claimed invention(s). Instead, this brief description only presents general embodiments and corresponding points of novelty over conventional techniques. For additional summary, details, and/or possible perspectives (permutations) of the invention(s), the reader is directed to the Detailed Description section and corresponding figures of the present disclosure as further discussed below.

BRIEF DESCRIPTION OF THE DRAWINGS

FIGS. 6A, 6B, and 6C are example perspective view diagrams illustrating a sequence of inserting tabs of a fluid pump assembly into corresponding loading guides and retraction of the corresponding loading guides to engage the fluid pump assembly to the fluid delivery system according to embodiments herein.

Figure 1:
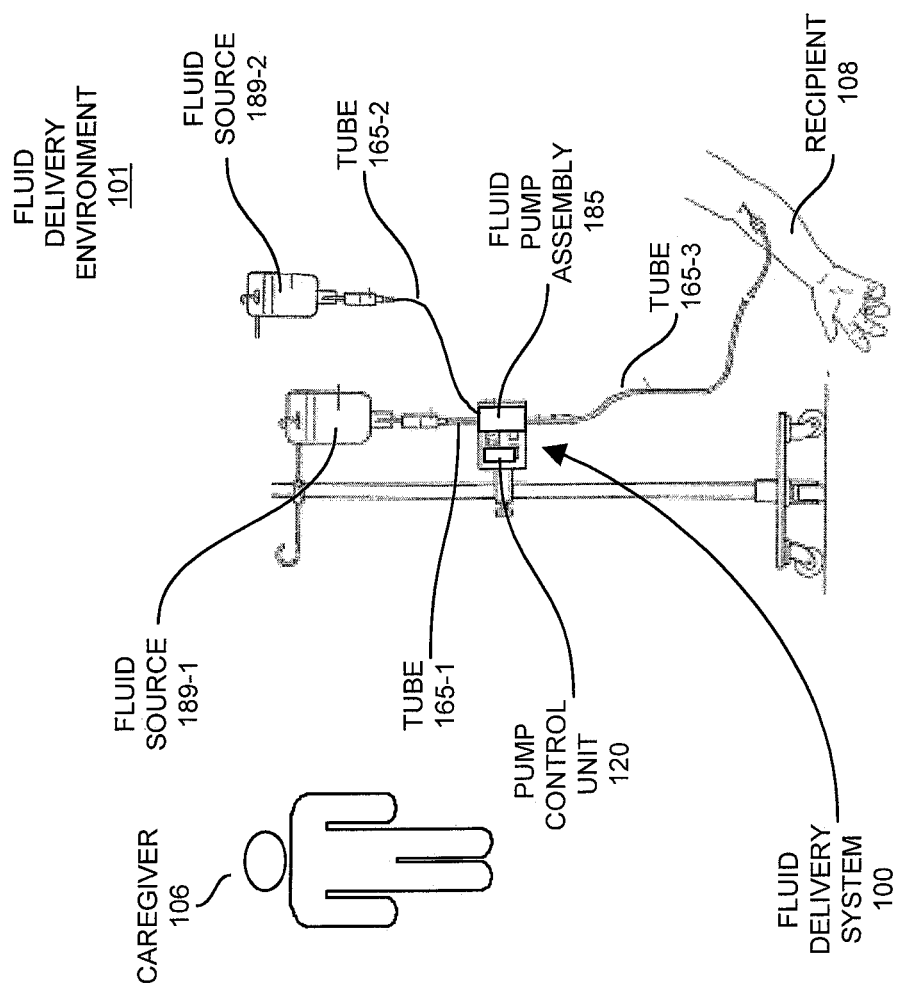
FIG. 1 is an example diagram of a fluid delivery environment according to embodiments herein.

The foregoing and other objects, features, and advantages of the invention will be apparent from the following more particular description of preferred embodiments herein, as illustrated in the accompanying drawings in which like reference characters refer to the same parts throughout the different views. The drawings are not necessarily to scale, with emphasis instead being placed upon illustrating the embodiments, principles, concepts, etc.

DETAILED DESCRIPTION AND FURTHER SUMMARY OF EMBODIMENTS

More specifically, FIG. 1 is an example diagram illustrating a fluid delivery environment and fluid delivery system according to embodiments herein.

As shown, the fluid delivery system 100 disposed in fluid delivery environment 101 includes a fluid source 189-1 (first fluid source), fluid source 189-2 (second fluid source), pump control unit 120, and disposable tube assembly. In one embodiment, the disposable tube assembly includes fluid pump assembly 185 such as a cassette as well as tube 165-1, tube 165-2, and tube 165-3.

Tube 165-1 conveys fluid from fluid source 189-1 to fluid pump assembly 185. Tube 165-2 conveys fluid from fluid source 189-2 to fluid pump assembly 185. Tube 165-3 conveys fluid from fluid pump assembly 185 to recipient 108.

In this example embodiment, fluid pump assembly 185 is already inserted in a corresponding cavity of pump control unit 120. Caregiver 106 programs the fluid delivery system 100 to deliver fluid at a desired rate to recipient 108.

In general, based on a desired flow rate set by caregiver 106, during operation, pump control unit 120 controls a corresponding pump resource (such as one or more diaphragm pumps), valves, etc., in fluid pump assembly 185 to deliver fluid from fluid sources 189 through tube 165-1, fluid pump assembly 185, and tube 165-3 to recipient 108. The recipient 108 can be any suitable type of entity such as a human, a pet, a container, etc.

Figure 2:
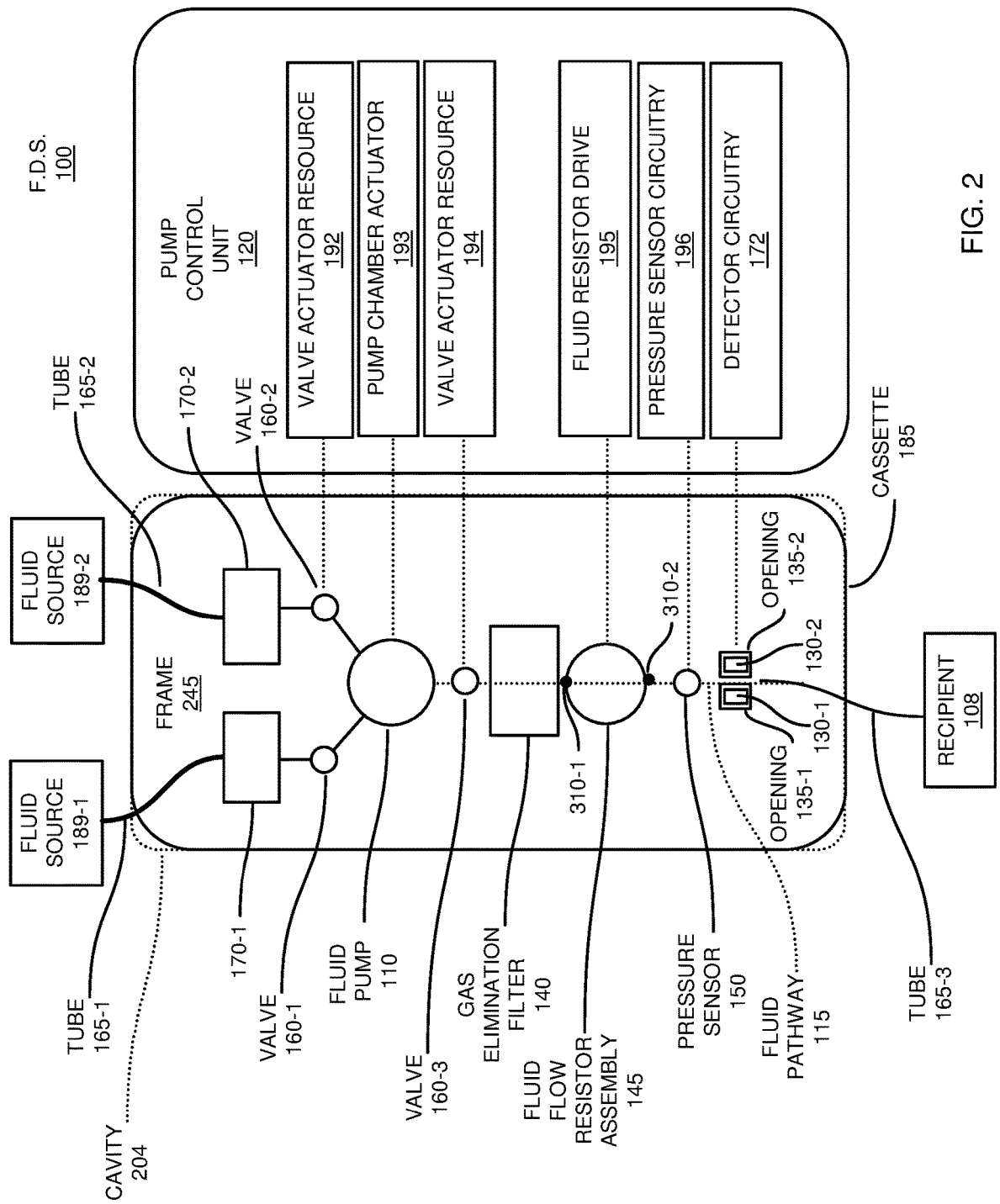
FIG. 2 is an example diagram illustrating detailed attributes of a fluid pump assembly according to embodiments herein.

FIG. 2 is an example diagram illustrating a disposable fluid pump assembly and corresponding pump control unit according to embodiments herein.

As previously discussed, embodiments herein include fluid pump assembly 185 that insertably fits into a corresponding cavity 204 of fluid delivery system 100.

In one embodiment, in addition to including tube 165-1 and tube 165-2, as previously discussed, note again that a respective disposable assembly can further include tube 165-3. As mentioned, a combination of resources including tube 165-1, tube 165-2, tube 165-3, and fluid pump assembly 185 represent an assembly such as a disposable tube set. As its name suggests, the disposable tube set can be thrown away after it is used to deliver a corresponding fluid to an entity such as recipient 108 (such as a patient).

The pump controller unit 120 can be used in conjunction with each new disposable tube set to deliver fluid to other patients. Thus, the pump controller unit 120 is reusable across multiple patients. However, as mentioned, each respective disposable tube set is typically used to deliver fluid to only one patient.

As shown and as previously discussed, insertion of fluid pump assembly 185 into the corresponding cavity 204 of the fluid delivery system 100 provides coupling between resources in the fluid pump assembly 185 and control resources in pump control unit 120.

For example, when the fluid pump assembly 185 is inserted into cavity 204 of the fluid delivery system 100, valve actuator resource 192 (e.g., a valve controller) becomes coupled to corresponding valves 160 (valve 160-1 and valve 160-2) in the fluid pump assembly 185.

During pump operation, valve actuator resource 192 in the pump control unit 120 controls settings of valves 160-1 and 160-2 to respective open and closed states, allowing and restricting a flow of fluid.

Further in this example embodiment, note that valve actuator resource 194 in the pump controller unit 120 controls opening and closing of valve 160-3 to control a flow of fluid along fluid pathway 115 to recipient 182.

The valve actuator resources in the pump controller unit 120 can control the respective valves 160 in any suitable manner depending on the type of the valves. For example, depending on the type of valves, via control input from the valve actuator resources in the pump control unit 120, the valves 160 can be electromechanically controlled, hydraulically controlled, pneumatically controlled, etc.

Thus, when pumping respective fluid from one or more fluid sources 189, the pump control unit 120 controls valves 160 to respective open and closed states as desired.

As a more specific example, to draw fluid from the first fluid source 189-1 through the primary inlet 170-1 into a respective pump chamber of fluid pump 110, the pump control unit 120 opens valve 160-1 and closes valve 160-2 and valve 160-3. While only valve 160-1 is open, the pump control unit 120 controls pump chamber actuator 193 to draw fluid through tube 165-1 into the pump chamber of fluid pump 110.

After drawing a desired or sufficient amount of fluid into the pump chamber of fluid pump 110, the pump control unit 120 closes valves 160-1 and valve 160-2 and opens valve 160-3. While only valve 160-3 is open, the pump control unit 120 controls pump chamber actuator 193 to force the fluid in the pump chamber fluid pump 110 downstream along fluid pathway 115.

Note further that embodiments herein can include switching between drawing fluids from the different fluid sources 189 and delivering such fluids to the recipient 108. For example, in a first pump cycle, the pump controller unit 120 can be configured to control valves 160 (valve 160-1, valve 160-2, valve 160-3) to deliver fluid from fluid source 189-1 to recipient 108 in a manner as previously discussed; in a second pump cycle, the pump controller unit 120 can be configured to control valves 160 to deliver fluid from fluid source 189-2 to recipient 108 in a similar manner as previously discussed; in a third pump cycle, the pump controller unit 120 can be configured to control valves 160 to deliver fluid from fluid source 189-1 to recipient 108 in a manner as previously discussed; in a fourth pump cycle, the pump controller unit 120 can be configured to control valves 160 to deliver fluid from fluid source 189-2 to recipient 108 in a similar manner as previously discussed; and so on.

Accordingly, a single fluid pump 110 (such as diaphragm pump) in fluid pump assembly 185 can be used to switch between delivering fluid from different sources 189 to a recipient 108. If desired, the fluid pump assembly 185 can be configured to include multiple fluid pumps instead of a single fluid pump 110.

As further shown, downstream in fluid pathway 115 with respect to valve 160-3, note that fluid pump assembly 185 can further include gas elimination filter 140.

In one embodiment, as shown, the gas elimination filter 140 is disposed upstream with respect to fluid flow resistor assembly 145. Disposing the gas elimination filter 140 upstream with respect to the fluid flow resistor assembly 145 ensures that the gas elimination filter 140 remains under positive pressure (e.g., a higher pressure than a pressure at a location monitored by pressure sensor resource 150 as discussed below) during fluid delivery.

As its name suggests, and as previously discussed, the gas elimination filter 140 disposed in fluid pump assembly 185 removes any air or gases from the fluid traveling downstream along fluid pathway 115 towards fluid flow resistor assembly 145. In one embodiment, the gas elimination filter 140 vents any detected gas out of the fluid pathway 115 into open atmosphere (open air as exhaust).

In accordance with further embodiments, fluid resistor drive 195 controls a degree to which the fluid flow resistor assembly 145 resists a corresponding flow of the fluid along fluid pathway 115 towards recipient 108. Increased resistance provided by the fluid flow resistor assembly 145 reduces a flow rate of fluid long pathway 115 to recipient 108. Decreased resistance provided by the fluid flow resistor assembly 145 increases a flow rate of fluid along pathway 115 to recipient 108.

Port 310-1 (such as an input port) of the fluid flow resistor assembly 145 receives fluid passing along fluid pathway 115 through gas elimination filter 140. Port 310-2 (such as an output port) of the fluid flow resistor assembly outputs respective fluid in fluid pathway 115 downstream towards pressure sensor resource 150.

In a similar manner as previously discussed, the fluid flow resistor assembly 145 can be controlled in any suitable manner. For example, the fluid flow resistor assembly 145 can be electromechanically controlled, hydraulically controlled, pneumatically controlled, etc., via fluid resistor drive 195.

In accordance with yet further embodiments, fluid pump assembly 185 further includes pressure sensor resource 150 disposed in fluid pathway 115 downstream with respect to fluid flow resistor assembly 145.

In one non-limiting example embodiment, the pressure sensor resource 150 monitors a pressure of fluid disposed and passing through a corresponding location along fluid pathway 115 as shown. Via pressure sensor circuitry 196 in communication with pressure sensor resource 150, a flow-control monitoring algorithm executed by the pump control unit 120 is able to determine a pressure of fluid delivered to the recipient 108 at a downstream location in fluid pathway 115 with respect to the fluid flow resistor assembly 145.

In one embodiment, the pressure sensor circuitry 196 in the pump control unit 120 detects when there is a blockage downstream that prevents delivery of corresponding fluid to a recipient 108. For example, in one embodiment, when the pressure sensor circuitry 196 detects that the pressure at the location monitored by pressure sensor resource 150 is above a threshold value, the pressure sensor circuitry 196 generates a corresponding signal indicating a blockage condition and/or inability to deliver fluid to the recipient 108. Detecting pressure below the threshold value generally indicates that there is no blockage downstream and that the fluid is being delivered through the fluid pathway 115 to the recipient 108, which is desired.

During pumping of fluid to recipient 108 via control of the fluid pump 110 as previously discussed, gas elimination filter 140 typically removes gas from the infusion line (fluid pathway 115) before it reaches the detector elements 130.

If the gas elimination filter 140 fails for some reason, and bubbles are detected by one or more detector elements 130-1 and 130-2 monitoring a flow of fluid through pathway 115, the bubble detector circuitry 172 generates a corresponding signal to pump control unit 120 to close the fluid flow resistor assembly 145 and/or valves 160 to stop fluid flow. The corresponding signal indicates to the pump control unit 120 to discontinue delivery of corresponding fluid to the recipient 108. This prevents any gas in the fluid in fluid pathway 115 from being delivered to recipient 108 in the event that the gas elimination filter 140 happens to fail to remove gas.

By further way of non-limiting example, in one embodiment, in response to receiving an indication that bubbles are detected in fluid being delivered to the corresponding recipient 108, the pump control unit 120 can be configured to close one or more valves such as valve 160-1, valve 160-2, valve 160-3 and/or deactivate fluid pump 110 to discontinue delivery of fluid to the recipient 108.

In accordance with further embodiments, fluid pumped assembly 185 includes a frame 245 (made of plastic or other suitable material) to retain resources such as valves 160, fluid pump 110, gas elimination filter 140, fluid flow resistor assembly 145, pressure sensor resource 150, openings 135, pathway 115, etc.

In one embodiment, the frame 245 is made of transparent material, facilitating a view of each of the above-mentioned resources. In other words, the caregiver 106 is able to see through the frame 245 and view the different resources such as valve 160-1, valve 160-2, fluid pump 110, valve 160-3, gas elimination filter 140, etc.

Thus, in summary, the frame 245 of fluid pump assembly 185 includes fluid pathway 115. As previously discussed, the fluid pathway 115 includes gas elimination filter 140 and a flow resistor 145. The gas elimination filter 140 is disposed in the fluid pathway 115 downstream of the fluid pump 110. The flow resistor 145 is disposed in the fluid pathway 115 downstream from the gas elimination filter 140. As previously discussed, further embodiments of the fluid pump assembly 185 can include a pressure sensor 150 as shown. Pressure sensor 150 monitors a pressure of fluid in the fluid pathway 115 at a location in the fluid pathway between the flow resistor 145 and the location of the fluid pathway 115 between the first detector element 130-1 and second detector element 130-2.

As further shown, the frame 245 of the fluid pump assembly 185 can include tab 275-1, tab 275-2, tab 275-3, and tab 275-4 (collectively, tabs 275). As further discussed herein, the tabs 275 facilitate coupling or mating of the fluid pump assembly 185 to the fluid delivery system 100.

Figure 3:
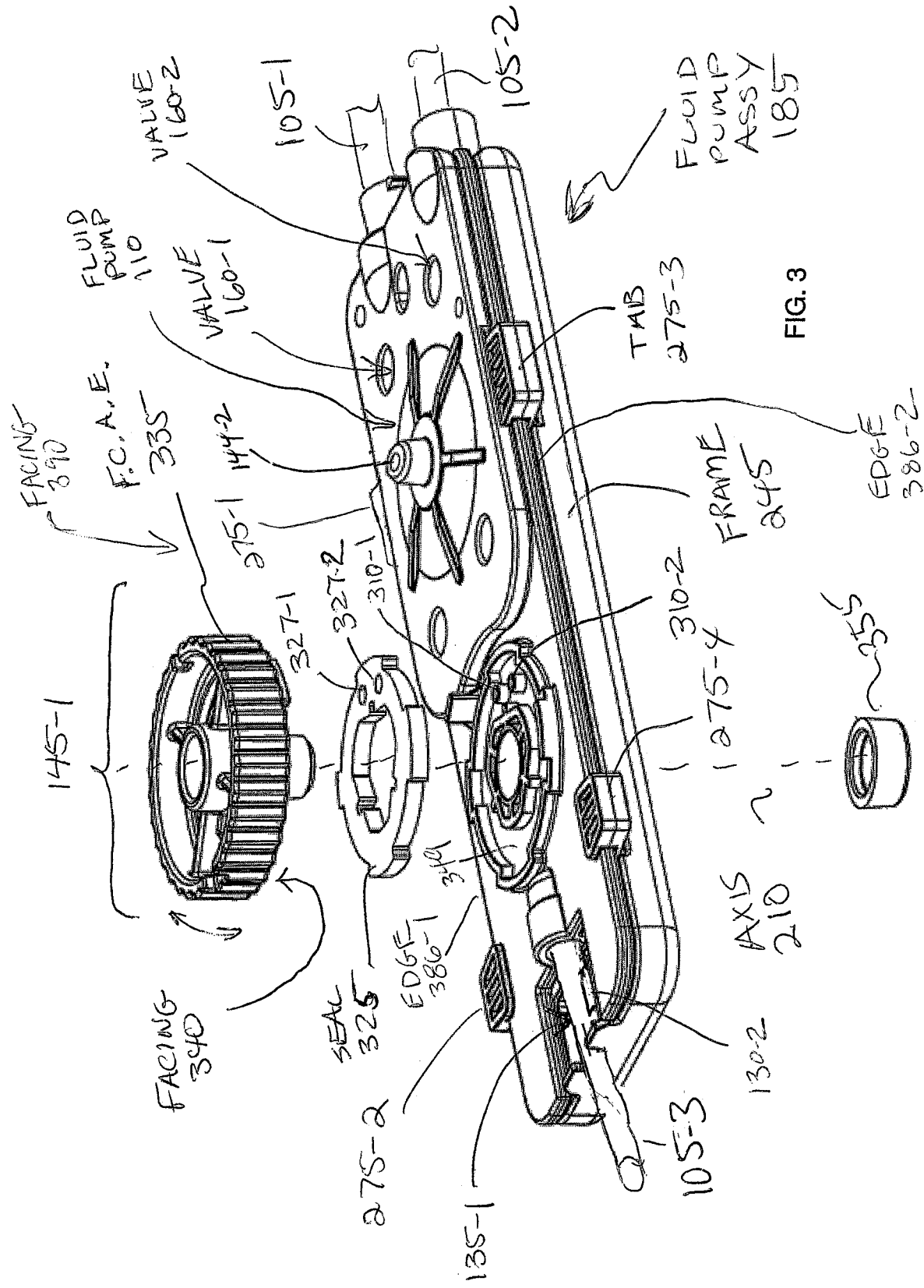
FIG. 3 is an example perspective view diagram illustrating a fluid pump assembly and corresponding exploded view of a fluid flow resistor mechanism according to embodiments herein.

FIG. 3 is an example perspective view diagram illustrating a fluid pump assembly and corresponding exploded view of a fluid flow resistor assembly according to embodiments herein.

In this example embodiment, the frame 245 of the fluid pump assembly 185 includes tabs 275 spaced apart from each other along respective edges of frame 245.

Note that use of spaced tabs is shown by way of non-limiting example embodiment only. If desired, the pair of tabs 275-3 and 275-4 disposed along a respective edge 386-2 of the frame 245 can be formed into a single tab along edge 386-2. For example, the spacing between tabs 275-3 and 275-4 can be filled in with appropriate material (such as transparent material) to form a single tab. Similarly, if desired, the spacing between tabs 275-1 and 275-2 can be filled in with appropriate material to form a single tab along edge 386-1.

In accordance with alternative embodiments, each of the edges 386 can include additional tabs. For example, edge 386-1 can include any number of one or more additional tabs disposed between or outside of tabs 275-1 and 275-2. Edge 386-2 can include any number of one or more additional tabs disposed between or outside of tabs 275-3 and 275-4.

Further in this example embodiment, the fluid flow resistor assembly 145-1 includes a first flow control assembly element 335 (such as a gear element), a second flow control assembly element (such as seal 325), port 310-1, port 310-2, and fastener 355. In one embodiment, the seal 325 is an elastomeric seal (a.k.a., rubber).

The seal 325 includes ports 327-1 and 327-2.

Note that port 310-1, port 310-2, port 327-1, and port 327-2 can be located at any suitable location with respect to flow control assembly element 335 and axis 210.

The first flow control assembly element 335 and ports 310 disposed in fluid pump assembly 185 can be made of rigid plastic or other suitable material. As shown, the ports 310 protrude from the respective surface of fluid pump assembly 185. Alternatively, the ports 310 can be flush with respect to a surface of the fluid pump assembly 185.

After installation, fastener 355 (such as formed via gluing, welding, snap-fit, etc.) secures flow control assembly element 335 to the fluid pump assembly 185, compressing facing 340 of the flow control assembly element 335 to a respective surface of seal 325. The opposite facing of seal 325 is compressed and in contact with the surface 349 of the fluid pump assembly 185.

Port 327-1 provides a fluid-tight pathway between port 310-1 of fluid pump assembly 185 and a first location on a respective surface of facing 340. Port 327-2 provides a fluid-tight pathway between port 310-2 and a second location on the respective surface of facing 340.

Further, as previously discussed, fluid pump assembly 185 includes fluid pump 110 (any suitable type of pump such as a diaphragm pump assembly). The pump control unit 120 controls settings of the respective valves 160 as well as a flow of gas (such as a negative pressure) to port 144-2 of the fluid pump 110 to draw fluid from one or more respective fluid sources 189 into a respective chamber fluid pump 110. Subsequent application of positive pressure to the port (while valves 160-1 and 160-2 are closed) pushes fluid in the chamber of the fluid pump 110 downstream along fluid pathway 115. Yet further, as previously discussed, fluid pathway 115 includes fluid flow resistor assembly 145-1 controlled by fluid resistor drive 195. In one embodiment, the fluid resistant drive 195 controls an angular or rotational orientation 375 of the flow control assembly element 335 with respect to axis 210 to control a respective flow of fluid further down fluid pathway 115 through tube 105-3 to recipient 108.

Additional details of controlling flow are discussed in related U.S. patent application Ser. No. 14/540,081 entitled "FLUID FLOW REGULATOR ASSEMBLY," filed on Nov. 13, 2014, the entire teachings of which are incorporated herein by this reference.

In one embodiment, as will be further discussed below, the port 310-1 receives fluid passing along fluid pathway 115 from gas elimination filter 140. Fluid received from port 310-1 and port 327-1 passes through a channel disposed between facing 340 of the flow control assembly element 335 and opposing facing of seal 325 to port 327-2 and port 310-2. Port 310-2 further conveys the fluid along the fluid pathway 115 of fluid pump assembly 185 towards pressure sensor 150 as previously discussed.

Note that, depending on the embodiment, the radial distance between axis 210 and a location of port 310-1 and port 327-1 and a location of port 310-2 and port 327-2 can be the same or different value as further discussed below.

In accordance with further embodiments, the flow control assembly element 335 is rotatable with respect to axis 210. The fluid resistor drive 195 controls an orientation of the flow control assembly element 335 (adjusting a positioning of the tapered channel with respect to the ports 310 and/or ports 327) to control a flow of fluid from the fluid source to the target recipient 108.

Figure 4:
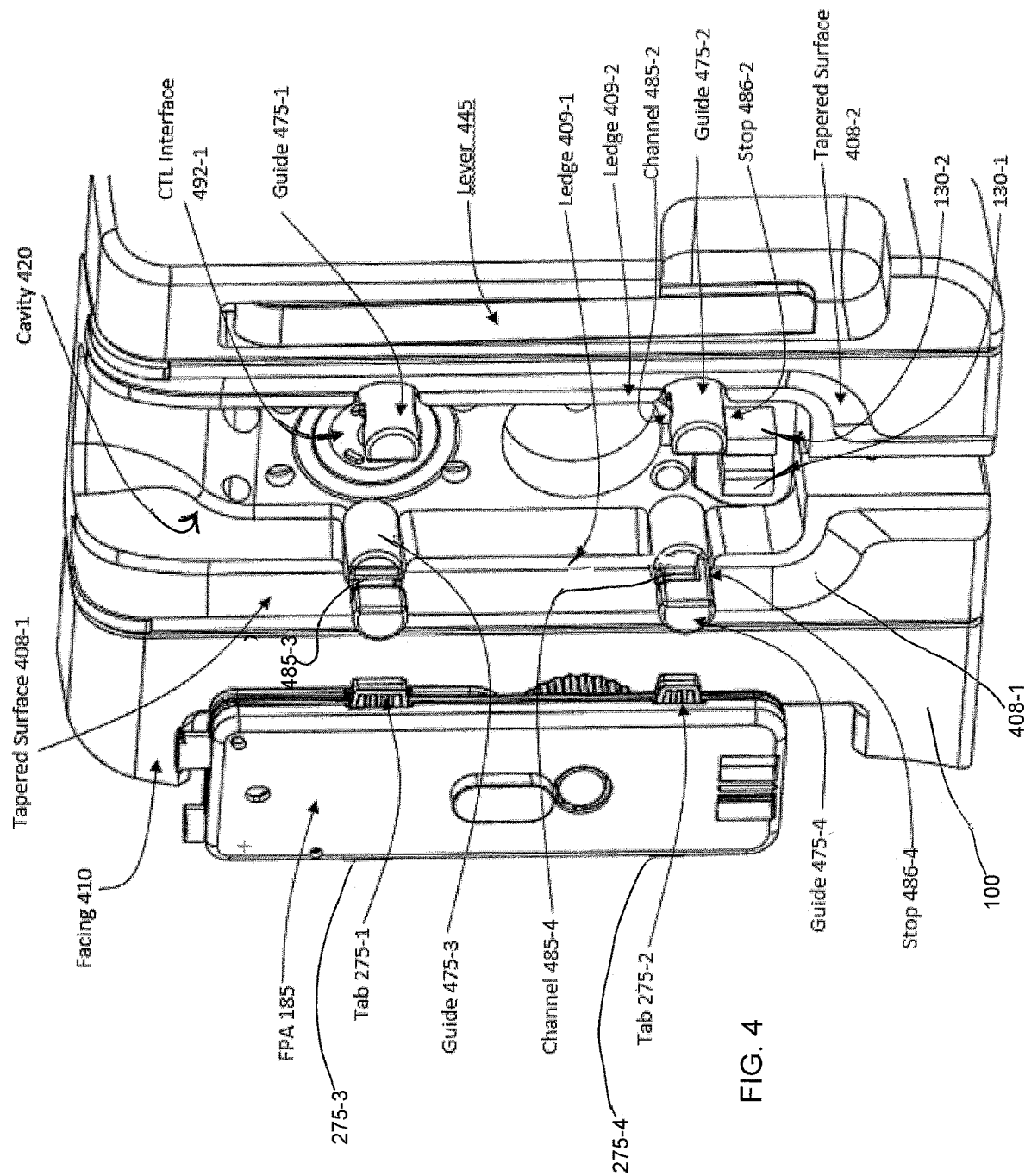
FIG. 4 is an example perspective view diagram illustrating a fluid pump assembly and corresponding fluid delivery system according to embodiments herein.

FIG. 4 is an example perspective view diagram illustrating a fluid delivery system and fluid pump assembly according to embodiments herein.

As shown, a surface or facing 410 of the fluid delivery system 100 can be configured to include cavity 420 for receiving the fluid pump assembly 185. Inside cavity 420 resides control interface 492 (control interface 492-1, control interface 492-2, etc.). If desired, as an alternative to residing in cavity 420, control interface 492 can reside directly on a surface of the fluid delivery system 100, outside a cavity.

Additionally, as shown, the fluid delivery system 100 can be configured to further include multiple loading guides 475 (e.g., loading guide 475-1, loading guide 475-2, loading guide 475-3, and loading guide 475-4) that retract into facing 410 of the fluid delivery system 100 in accordance with input from a respective caregiver 106. FIG. 4 illustrates the loading guides 475 in a fully extended (protruding) state prior to being retracted into the fluid delivery system 100.

In one embodiment, the multiple loading guides 475 are disposed at locations around a periphery of cavity 420 (such as in-line with edges 409) disposed on facing 410 of the fluid delivery system 100. Note again that depending upon the embodiment, control interface 492 for controlling the fluid pump assembly 185 can reside inside or outside of cavity 420.

As further shown, the cavity 420 includes tapered surface 408-1 and tapered surface 408-2. The tapered surfaces 408 help to center the fluid pump assembly 185 with respect to the cavity 420. That is, when the user moves the fluid pump assembly 185 for insertion into cavity 420, the tapered surface 408-2 serves to guide the tab 275-1 and tab 275-2 to come in contact with ledge 409-2; the tapered surface 408-1 serves to guide the tab 275-3 and tab 275-4 come in contact with ledge 409-1. Thus, presence of the ledges 409 in the cavity 420 and tabs 275 on the fluid pump assembly 185 prevent insertion of the flow pump assembly into cavity 420.

In one embodiment, the width between ledge 409-1 and ledge 409-2 is chosen to be substantially equal to a width across frame 245 between tab 275-2 and tab 275-4.

The tabs 275 on frame 245 slide along the axial lengths of ledges 409 such that the ledges 409 serve to guide the respective tabs 275 into channels 485 of the guides 475. In other words, when the loading guides 475 are extended outward from cavity 420 as shown in FIG. 4, an inner surface of channel 485-3 (associated with loading guide 475-3) and an inner surface of channel 485-4 (associated with loading guide 475-4) substantially align with the surface of ledge 409-1. Similarly, when the loading guides 475 are extended outward from cavity 420 as shown in FIG. 4, an inner surface of channel 485-1 (associated with loading guide 475-1) and an inner surface of channel 485-2 (associated with loading guide 475-2) substantially align with the surface of ledge 409-2.

Figure 5:
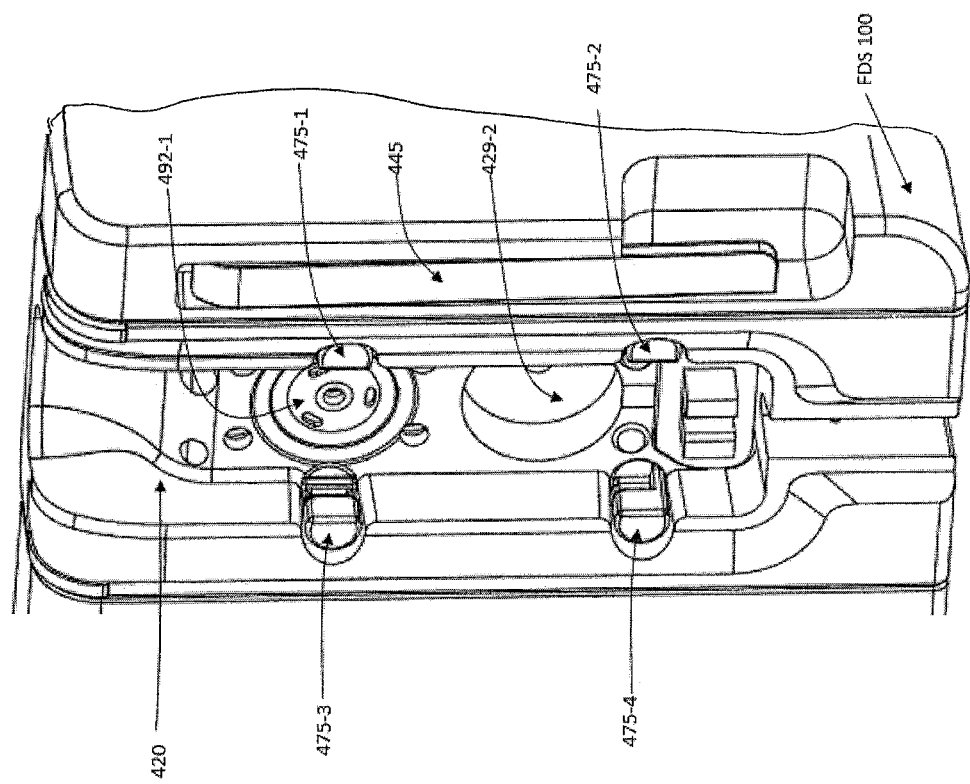
FIG. 5 is an example diagram illustrating retraction of loading guides into a fluid delivery system according to embodiments herein.

As previously discussed, inward movement of the loading guides 475 can be controlled by a respective resource such as a lever 445 of the fluid delivery system 100. For example, as further discussed herein, movement of the lever 445 to an open position causes the loading guides 475 to protrude from fluid delivery system 100 as shown in FIG. 4; movement of the lever 445 from the open position to a closed position causes the loading guides to retract into the fluid delivery system 100 (as shown in FIG. 5). Accordingly, embodiments herein can include a user-controlled lever resource 445 in mechanical communication with the multiple loading guides 475; the lever resource 445 controls movement of the multiple loading guides 475.

Each of the loading guides 475 can include a respective channel to receive a tab disposed on the fluid pump assembly 185. For example, as shown, guide 475-1 includes channel 485-1 to receive tab 275-1; guide 475-2 includes channel 485-2 to receive tab 275-2; guide 475-3 includes channel 485-3 to receive tab 275-3; and guide 475-4 includes channel 485-4 to receive tab 275-4.

As further shown, each of one or more of the tabs 275 can include a respective stop to prevent further sliding of the tab through a respective channel. For example, in one embodiment, the channel 485-4 of guide 475-4 includes stop 486-4; the channel 485-2 of opposing guide 475-2 includes stop 486-2.

As will be discussed further below, the stops 486 facilitate alignment of fluid pump assembly 185 with respect to control interface 492 disposed in cavity 420. More specifically, the stops 486 facilitate alignment of the port 144-2 with the center of corresponding control interface 492-1; stops 486 align the fluid control assembly element 335 with control interface 492-2; and so on. Accordingly, sliding of tabs 275 along respective ledges 409 into respective channels 485 of the loading guides 475 aligns the fluid pump assembly 185 for insertion into the cavity 420.

Subsequent to placement of the tabs 275 into the loading guides 475, prior to retracting of the loading guides into the fluid delivery system 100 using lever 445, respective spacings between the multiple loading guides 475 and pairs of tabs 275 provides the caregiver 106 a substantially unobstructed view of inserting the fluid pump assembly 185 into the cavity 420.

In one embodiment, the multiple loading guides 475 slidably retract in unison to support substantially orthogonal insertion of the fluid pump assembly 185 into the cavity 420 of the fluid delivery system 100. In one embodiment, sidewalls of the cavity 420 further facilitate: matable alignment of the port 144-2 with corresponding control interface 492-1 in cavity 420, matable alignment of the fluid control assembly element 335 with control interface 492-2 in cavity 420; and so on.

FIG. 5 is an example diagram illustrating retraction of the loading guides into the fluid delivery system according to embodiments herein.

As shown, movement of the lever resource 445 to be flush with respect to a surface of the fluid delivery system 100 causes the loading guides 475 to retract into the fluid delivery system 100. In this example, for purposes of illustrating movement of the guides 475, the lever resource 445 was moved to the closed position without insertion of a respective fluid pump assembly 185 in guides 475.

As previously discussed, the multiple loading guides 475 can be configured to slidably retract in unison to support substantially orthogonal insertion of a fluid pump assembly 185 into the cavity 420 of the fluid delivery system 100

Figure 6B:
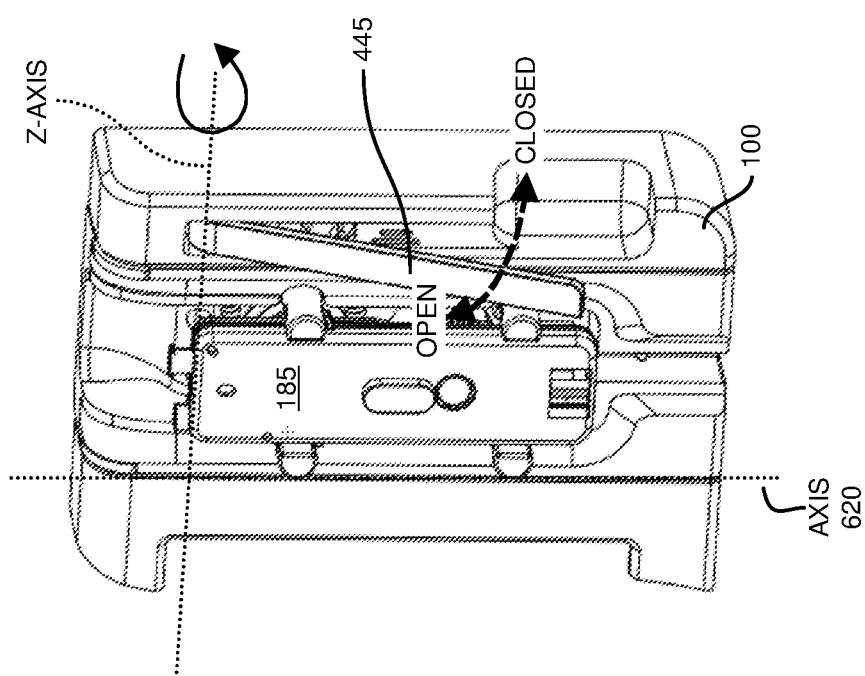
Figure 6C:
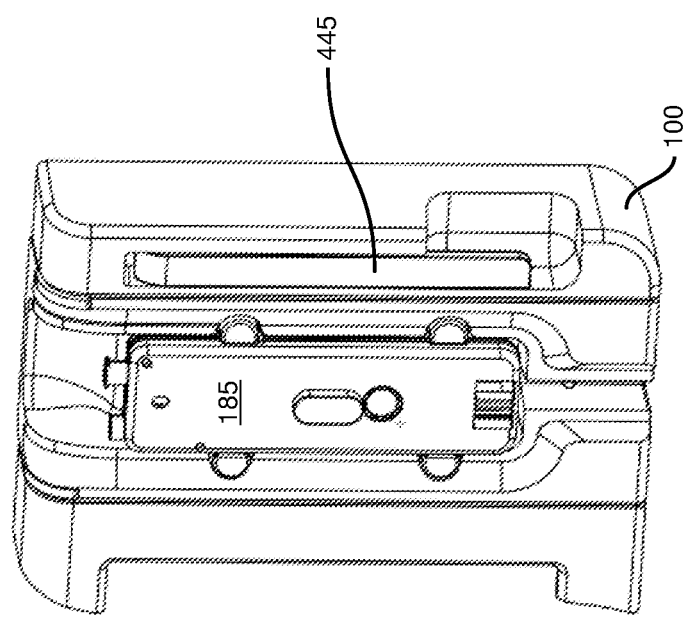

FIGS. 6A, 6B, and 6C are example perspective view diagrams illustrating a sequence of inserting tabs of a fluid pump assembly into corresponding loading guides and retraction of the corresponding loading guides to engage the fluid pump assembly to the fluid delivery system according to embodiments herein.

As shown in FIG. 6A, while lever resource 445 is in an open position pulled away from the fluid delivery system 100, a respective caregiver 106 slides the frame 245 of the fluid pump assembly 185 along axis 610 and ledges 409 to move tabs 275 into respective channels 485 of loading guides 475.

As shown in FIG. 6B, subsequent to sliding of the tabs 275 into respective channels 485 of the loading guides 475, the caregiver 106 pushes on lever resource 445. As previously discussed, this causes the loading guides 475 to retract into the fluid delivery system 100. Because the tabs 275 reside in respective channels 485 of the loading guides 475, retraction of the loading guides 475 causes: insertion of the fluid pump assembly 185 into respective cavity 420; mating of port 144-2 to the control interface 492-1; and coupling of fluid control assembly element 335 to control interface 492-2.

FIG. 6C illustrates final insertion of the fluid pump assembly 185 into cavity 420. At such time, when the fluid pump assembly 185 is fully inserted into the cavity 420, the pump control unit 120 in fluid delivery system 100 is able to control a flow of fluid through the fluid pathway 115 of the fluid pump assembly 185. More specifically, valve actuator resource 192 is able to control valve 160-1 and valve 160-2; pump chamber actuator 193 is able to control fluid pump 110; valve actuator resource 194 is able to control valves 160-3; fluid resistor drive 195 is able to control fluid flow resistor assembly 145; pressure sensor circuitry 196 is able to sense pressure associated with pressure sensor resource 150 disposed in fluid pathway 115; detector circuitry 172 is able to detect the flow of gas bubbles through tube 165-3.

Figure 7C:
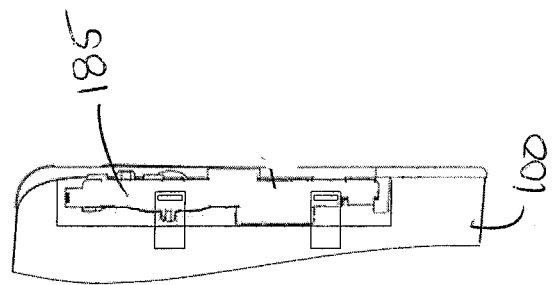
FIGS. 7A, 7B, and 7C are example side view diagrams illustrating a sequence of engaging a fluid pump assembly to a facing of a fluid delivery system according to embodiments herein.
Figure 7B:
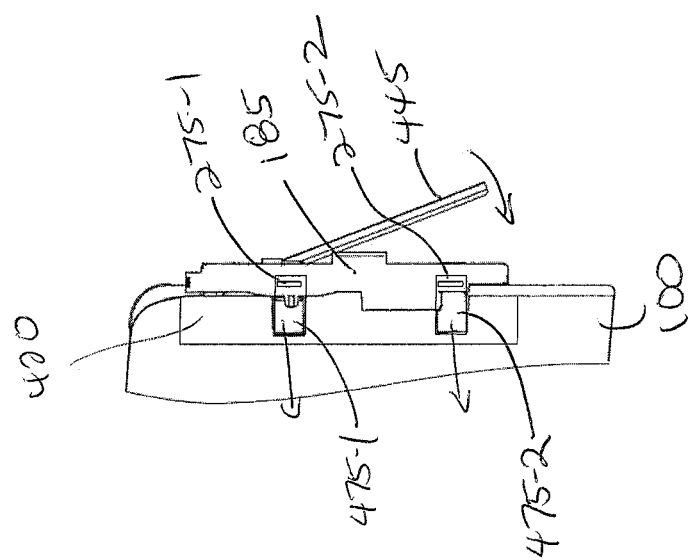
Figure 7A:
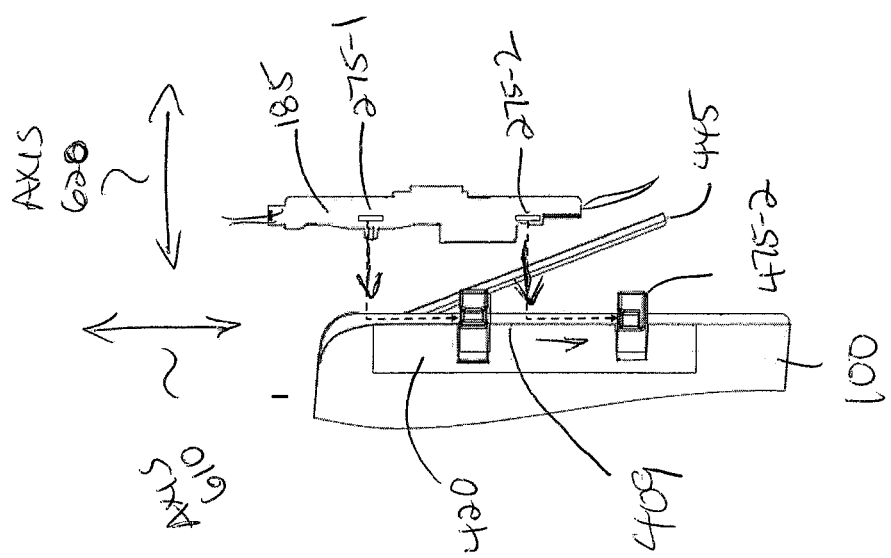

FIGS. 7A, 7B, and 7C are example side view diagrams illustrating a sequence of engaging a fluid pump assembly to a facing of a fluid delivery system according to embodiments herein.

As shown in FIG. 7A, while lever resource 445 is in an open position pulled away from the fluid delivery system 100, a respective caregiver 106 moves frame 245 as shown along axis 620. When the tabs 275 come in contact with the ledges 409, the caregiver 106 then slides the frame 245 of the fluid pump assembly 185 along axis 610 and ledges 409 (in a downward direction) to move respective tabs 275 of the frame 245 into respective channels 485 of loading guides 475. In one embodiment, axis 620 is substantially orthogonal to axis 610.

As previously discussed, a portion of a peripheral edge of the cavity 420 includes tapered surfaces 408 to facilitate centering of the fluid pump assembly 185 with respect to cavity 420 as the user moves the fluid pump assembly 185 towards cavity 420. The caregiver 106 then slides tabs 275 along surfaces of ledges 409 into respective channels 485 of the loading guides 475.

As shown in FIG. 7B, subsequent to sliding of the tabs 275 into respective channels 485 of the loading guides 475, the caregiver 106 pushes on lever resource 445 as shown. As previously discussed, this causes the loading guides 475 to retract into the fluid delivery system 100. Because the tabs 275 reside in respective channels 485 of the loading guides 475, retraction of the loading guides 475 causes insertion of the fluid pump assembly 185 into respective cavity 420.

FIG. 7C illustrates final insertion of the fluid pump assembly 185 into cavity 420. As previously discussed, at such time when the fluid pump assembly 185 is fully inserted into the cavity 420, the pump control unit 120 in fluid delivery system 100 is able to control a flow of fluid through the fluid pathway 115 of the fluid pump assembly 185. More specifically, when the fluid pump assembly 185 is fully inserted into cavity 420, valve actuator resource 192 controls valve 160-1 and valve 160-2; pump chamber actuator 193 is able to control fluid pump 110; valve actuator resource 194 controls valves 160-3; fluid resistor drive 195 controls fluid flow resistor assembly 145; pressure sensor circuitry 196 senses pressure associated with pressure sensor resource 150 disposed in fluid pathway 115; detector circuitry 172 detects the flow of gas bubbles through tube 165-3.

Figure 9:
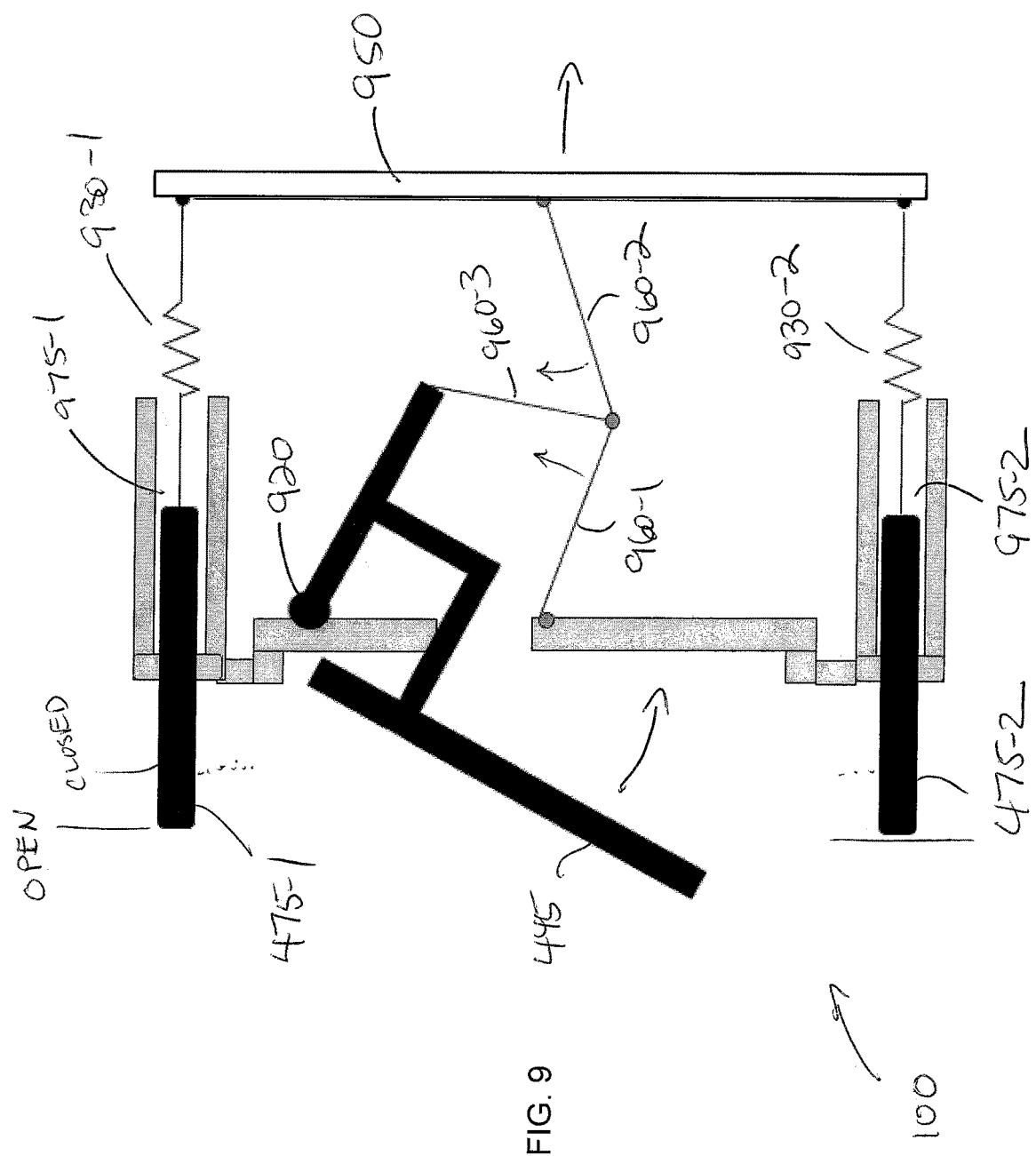
FIGS. 9 and 10 are example functional side view diagrams illustrating translation of rotational motion into substantially simultaneous retraction of the loading guides according to embodiments herein.
Figure 10:
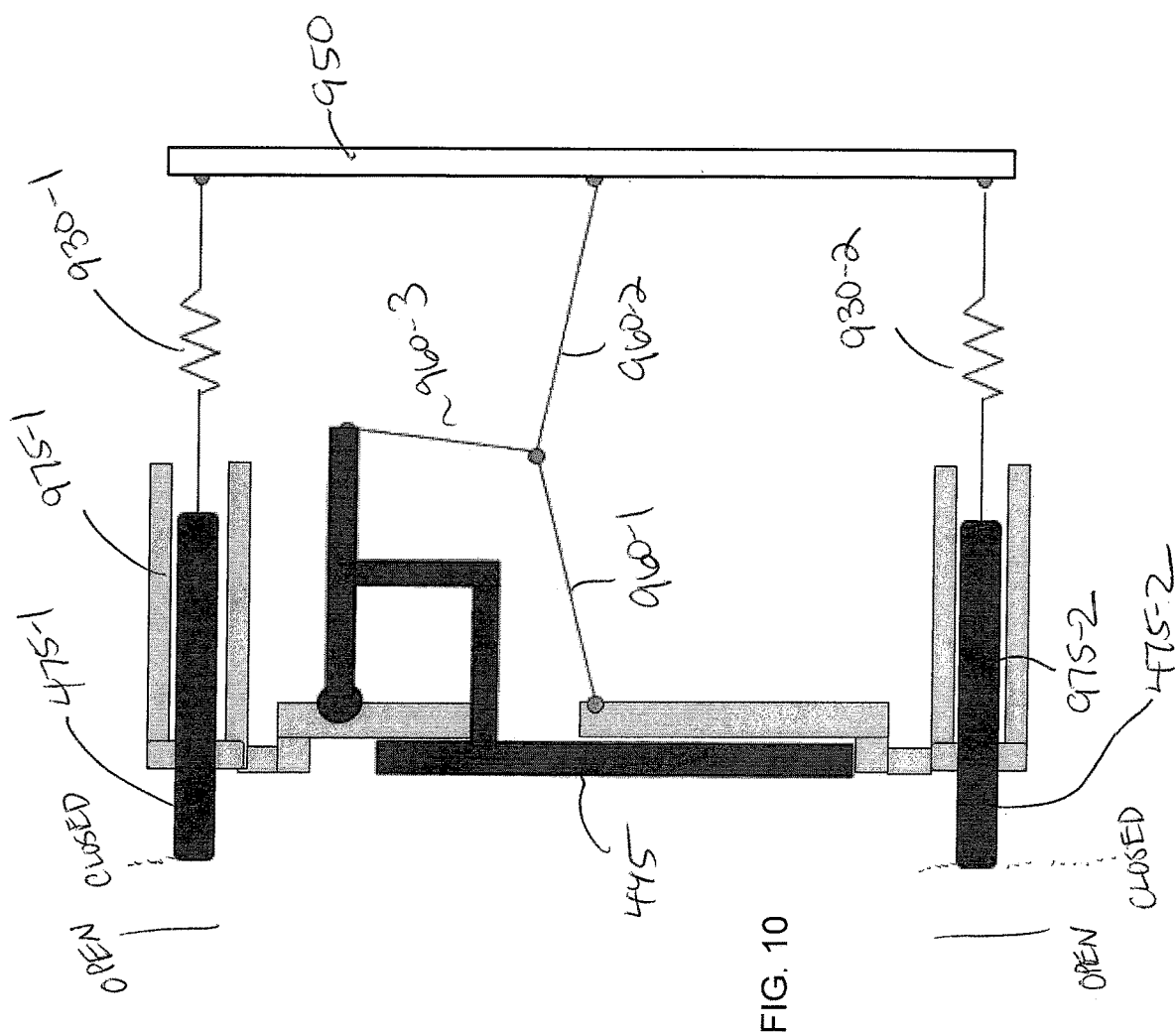

FIGS. 9 and 10 are example functional side view diagrams illustrating conversion of rotational motion into translational or parallel motion of the loading guides according to embodiments herein.

As shown in FIG. 9, the fluid delivery system includes lever resource 445, linkage 960-1, linkage 960-2, linkage 960-3, rigid member 950, spring resource 930-1, spring resource 930-2, and loading guides 475. In this example embodiment, loading guide 475-1 resides and slides within track 975-1 (such as a linear bearing). Loading guide 475-2 resides and slides within track 975-2 (such as a linear bearing).

In one embodiment, each of the linkages 960-1, 960-2, 960-3, etc., are made from rigid material.

To retract the loading guides 475 into respective tracks 975, after inserting the fluid pump assembly 185 into the respective holding channels of the loading guides 475, the user pushes on lever resource 445, causing it to move member 950 to the right as shown. For example, lever resource 445 rotates about pivot 920 and/or axis z as previously discussed. Such motion of the lever resource 445 causes linkage 960 to move member 950 to the right. This causes the member 950 to exert a pulling force on each of the spring resources 930-1 and 930-2, causing movement of the distal tips of the loading guides 475-1 and 475-2 to move from the open position to the closed position. Thus, the lever resource 445 controls movement of the loading guides 475 along respective tracks 975.

FIG. 10 illustrates a corresponding position of member 950 as well as springs 930 and loading guides 475 after the lever resource 445 has been pushed to the full closed position. At such time, the member 950 is furthest away from lever resource 445.

Movement of the member 950 to this far right position causes the spring resource 930-1 to retract loading guide 475-1 into the fluid delivery system 100 to the closed position. Additionally, movement of the member 950 to this far right position causes the spring resource 930-2 to retract loading guide 475-2 into the fluid delivery system 100 to the closed position. In such an instance, as previously discussed, the loading guides 475 fully draw the fluid pump assembly 185 into cavity 420 of the fluid delivery system 100.

To remove the fluid pump assembly 185 from cavity 0420, the user (such as caregiver 106) pulls on lever resource 445 away from the fluid delivery system 100. This causes linkage 960 to move member 950 to the left. Movement of member 950 to the left causes the spring resources 930 to apply a corresponding pushing force on loading guides 475 to move them to the open position.

Accordingly, a combination of the linkage 960, member 950, and spring resources act as a translator mechanism. For example, the linkage 960 receives a force to pull in or push out loading guides 475 based on force from rotational movement of the user-controlled lever resource 445 with respect to the pivot 920 (or z-axis). During operation, the translator mechanism (combination of linkage 960, member 950, and spring resources 930) converts the force received from rotational movement of the user-controlled lever resource 445 into substantially orthogonal translational motion of the loading guides 475 (in or out depending on a motion of the lever resource 445) with respect to the control interface 485 disposed in cavity 420.

Note that inclusion of multiple spring resources 930 (such as one spring resource for each loading guide) is shown by way of non-limiting example only. In certain embodiments, a single spring resource can be used to provide a distribution of a force (push or pull) to each of the loading guides 475 based on movement of the lever resource 445.

In one embodiment, compliance in the pins (loading guides 475) allows the system to more tightly control proper alignment of the cassette (fluid pump assembly 185) into the cavity 420 during insertion. Additionally, in one embodiment, compliance can also allow the system to control the maximum force placed on the tabs 275 and respective cassette during loading and operating.

Figure 11A:
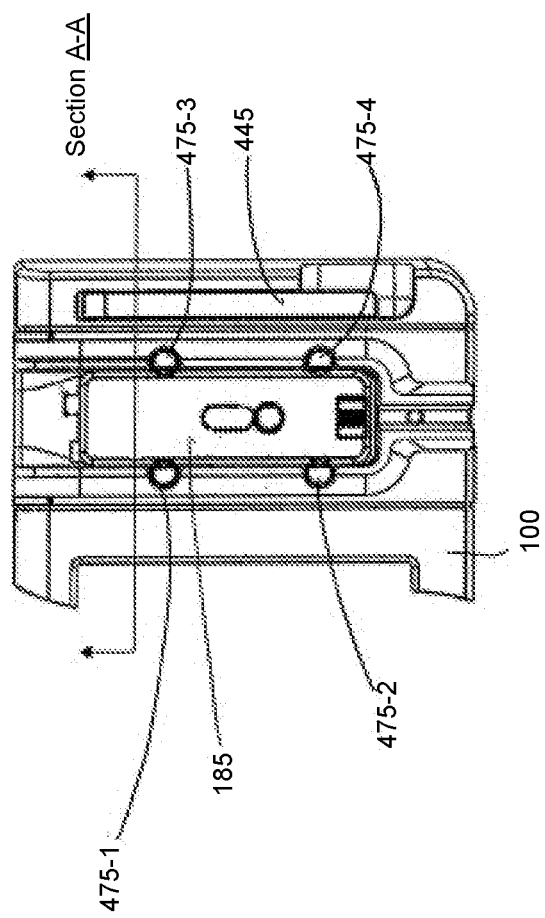
FIG. 11A is an example perspective view diagram of a fluid delivery system according to embodiments herein.

FIG. 11A is a perspective view diagram of a fluid delivery system according to embodiments herein. As previously discussed, fluid pump assembly 185 retracts into cavity 420 via movement and control of respecting loading guides 475.

Figure 11B:
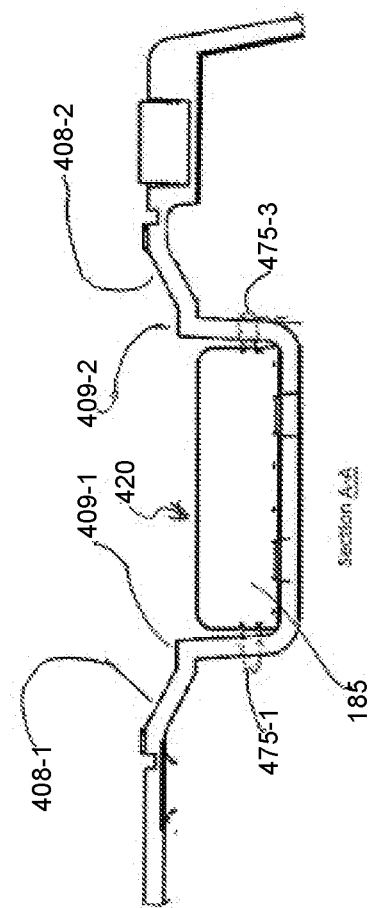
FIG. 11B is a cross-sectional view diagram (of section A-A) illustrating attributes of ledges and tapered surfaces of the fluid delivery system according to embodiments herein.

FIG. 11B is a cross-sectional view diagram (of section A-A) illustrating attributes of ledges and tapered surfaces of the fluid delivery system according to embodiments herein. As shown, and as previously discussed, tabs 275-1 and 275-3 extend beyond a width of ledges 409-1 and 409-2. Tapered surfaces 408-1 and 408-2 facilitate guidance of the tabs 275 of the fluid pump assembly 185 into ledges 409. Subsequent to moving tabs 275 into respective channels of loading guides 475, loading guides 475 retract to apply a force on tabs 475, drawing the fluid pump assembly 185 into cavity 420.

Figure 8:
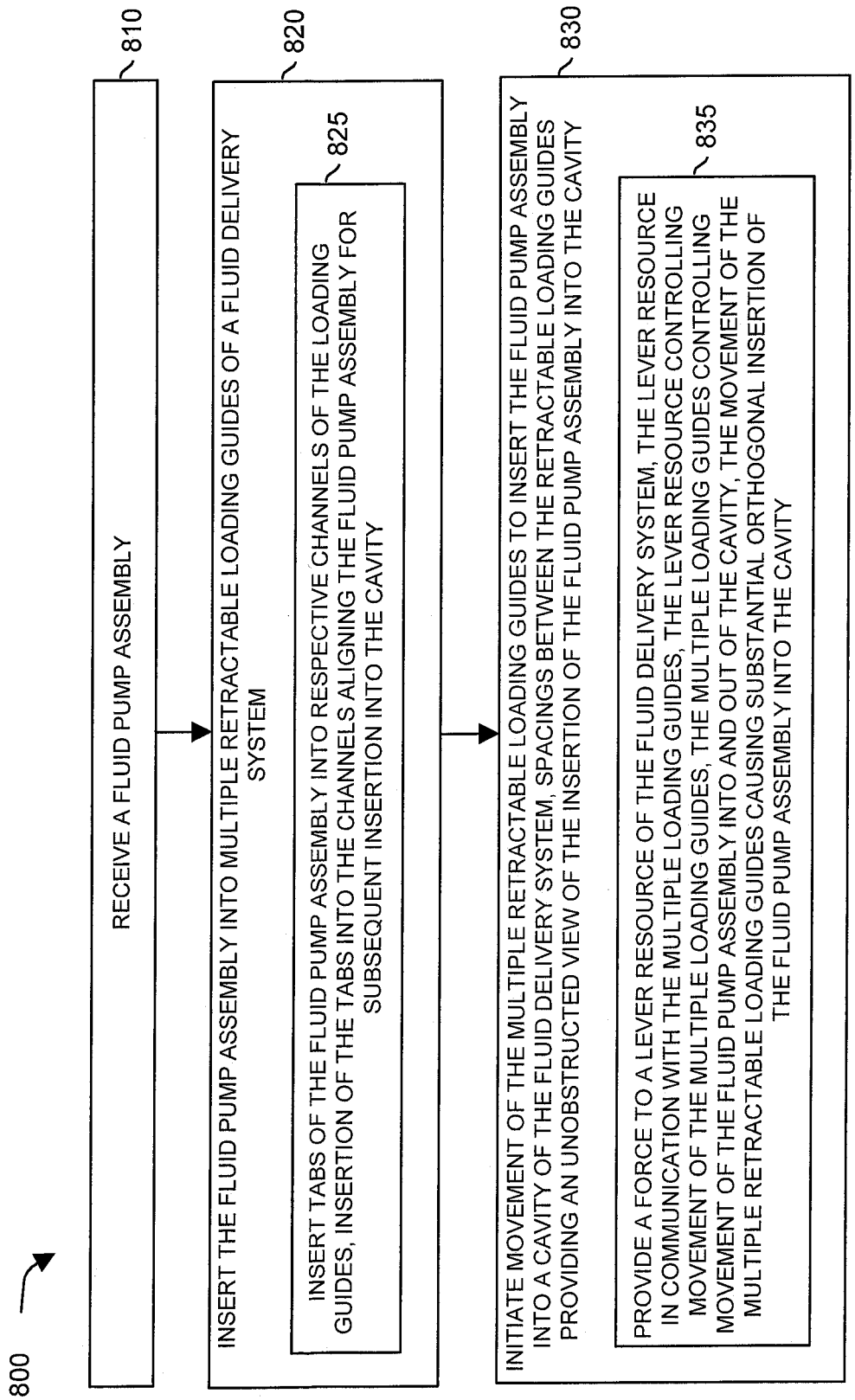
FIG. 8 is an example diagram illustrating a method according to embodiments herein.

Further functionality supported by the different resources will now be discussed via the flowchart in FIG. 8. Note that the steps in the flowcharts below can be executed in any suitable order. More specifically, FIG. 8 is a flowchart 800 illustrating an example method according to embodiments herein. Note that there may be some overlap with respect to concepts as discussed above.

In processing block 810, a caregiver 106 receives a fluid pump assembly 185.

In processing block 820, the caregiver 106 inserts the fluid pump assembly 185 into multiple retractable loading guides 275 protruding from the facing of fluid delivery system 100.

In sub-processing block 825, the caregiver 106 inserts tabs 275 of the fluid pump assembly 185 into respective channels of the loading guides. Insertion of the tabs into the channels aligns the fluid pump assembly 185 for subsequent insertion into the cavity 204.

In processing block 830, the caregiver 106 initiates movement of the multiple retractable loading guides, resulting in insertion of the fluid pump assembly 185 into the cavity 204 of the fluid delivery system 100. Spacings between the retractable loading guides provides the caregiver 106 an unobstructed view of the insertion of the fluid pump assembly 185 into the cavity 204.

In sub-processing block 835, via application of a force to the lever resource in communication with the multiple loading guides, the caregiver 106 controls movement of the multiple loading guides 475. Because the tabs 275 of the fluid pump assembly 185 are disposed in channels of the multiple loading guides 475, movement of the multiple loading guides 275 causes movement of the fluid pump assembly 185 into and out of the cavity 204 depending upon whether the caregiver 106 pushes the lever resource 445 in or pulls the lever resource 445 out. As previously discussed, in one embodiment, the movement of the multiple retractable loading guides 475 causes substantial orthogonal insertion of the fluid pump assembly into the cavity 204.

Note again that techniques herein are well suited for use in any suitable type of fluid delivery systems. However, it should be noted that embodiments herein are not limited to use in such applications and that the techniques discussed herein are well suited for other applications as well.

Based on the description set forth herein, numerous specific details have been set forth to provide a thorough understanding of claimed subject matter. However, it will be understood by those skilled in the art that claimed subject matter may be practiced without these specific details. In other instances, methods, apparatuses, systems, etc., that would be known by one of ordinary skill have not been described in detail so as not to obscure claimed subject matter. Some portions of the detailed description have been presented in terms of algorithms or symbolic representations of operations on data bits or binary digital signals stored within a computing system memory, such as a computer memory. These algorithmic descriptions or representations are examples of techniques used by those of ordinary skill in the data processing arts to convey the substance of their work to others skilled in the art. An algorithm as described herein, and generally, is considered to be a self-consistent sequence of operations or similar processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has been convenient at times, principally for reasons of common usage, to refer to such signals as bits, data, values, elements, symbols, characters, terms, numbers, numerals or the like. It should be understood, however, that all of these and similar terms are to be associated with appropriate physical quantities and are merely convenient labels. Unless specifically stated otherwise, as apparent from the following discussion, it is appreciated that throughout this specification discussions utilizing terms such as "processing," "computing," "calculating," "determining" or the like refer to actions or processes of a computing platform, such as a computer or a similar electronic computing device, that manipulates or transforms data represented as physical electronic or magnetic quantities within memories, registers, or other information storage devices, transmission devices, or display devices of the computing platform.

While this invention has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting. Rather, any limitations to the invention are presented in the following claims.

We claim:

1. A fluid delivery system comprising:
   a cavity in which to receive a fluid pump assembly;
   a pump control interface disposed in the cavity, the pump control interface operable to control the fluid pump assembly; and
   multiple retractable loading guides protruding from the cavity, the multiple retractable loading guides operable to retain and align the fluid pump assembly, movement of the multiple retractable loading guides further operable to matably contact the aligned fluid pump assembly to the pump control interface in the cavity;
   wherein the multiple retractable loading guides include corresponding channels in which to retain tabs of the fluid pump assembly, the corresponding channels of the multiple retractable loading guides operable to align the fluid pump assembly for insertion into the cavity;
   wherein the tabs protrude from edges of the fluid pump assembly; and
   wherein the cavity includes a tapered surface operative to guide the multiple tabs to a pair of ledges in the cavity, the multiple tabs being slidable along the pair of ledges into the corresponding channels of the multiple retractable loading guides.

2. The fluid delivery system as in claim 1 further comprising:
   a lever resource in communication with the multiple retractable loading guides, movement of the lever resource producing the movement of the multiple retractable loading guides.

3. The fluid delivery system as in claim 2 further comprising:
   at least one spring resource disposed between the lever resource and the multiple retractable loading guides, the at least one spring resource facilitating conveyance of a received force from the lever resource to the multiple retractable loading guides, the received force operative to control movement of the fluid pump assembly into the cavity.

4. The fluid delivery system as in claim 1, wherein the multiple retractable loading guides are spaced apart from each other and slidably retract in unison to support substantially orthogonal insertion of the fluid pump assembly into the cavity.

5. The fluid delivery system as in claim 4, wherein the multiple retractable loading guides are disposed at locations around a periphery of the cavity.

6. The fluid delivery system as in claim 1, wherein the movement of the multiple retractable loading guides is orthogonal with respect to a facing of the fluid delivery system.

7. The fluid delivery system as in claim 1, wherein the corresponding channels of the multiple retractable loading guides receive the tabs of the fluid pump assembly in a first direction, which is orthogonal to a second direction in which the multiple retractable loading guides move the fluid pump assembly into the cavity.

8. The fluid delivery system as in claim 1, wherein the multiple retractable loading guides are operable to at least temporarily retain the fluid pump assembly at a position external to the cavity prior to insertion of the fluid pump assembly into the cavity.

9. The fluid delivery system as in claim 1, wherein the multiple retractable loading guides protrude from a facing of the fluid delivery system to receive and retain the fluid pump assembly; and wherein a number of tabs disposed on edges of the fluid pump assembly matches a number of the multiple retractable loading guides protruding from the cavity.

10. The fluid delivery system as in claim 9, wherein each of the multiple retractable loading guides protrude in a same orthogonal direction with respect to the facing of the fluid delivery system.

11. The fluid delivery system as in claim 1, wherein the tabs include: i) a first set of tabs disposed on a first edge of the fluid pump assembly, and ii) a second set of tabs disposed on a second edge of the fluid pump assembly.

12. The fluid delivery system as in claim 11, wherein the pair of ledges includes:

a first ledge and a second ledge, the first ledge disposed on a first side of the cavity, the second ledge disposed on a second side of the cavity.

13. The fluid delivery system as in claim 1, wherein each of the multiple loading guides protrude in a same orthogonal direction with respect to a facing of the control interface.

14. A fluid delivery system comprising:

a cavity in which to receive a fluid pump assembly;

a pump control interface disposed in the cavity, the pump control interface operable to control the fluid pump assembly; and multiple retractable loading guides protruding from the cavity, the multiple retractable loading guides operable to retain and align the fluid pump assembly, movement of the multiple retractable loading guides further operable to matably contact the aligned fluid pump assembly to the pump control interface in the cavity;

wherein the multiple retractable loading guides include corresponding channels in which to retain tabs of the fluid pump assembly, the corresponding channels of the multiple retractable loading guides operable to align the fluid pump assembly for insertion into the cavity;

wherein the tabs include: i) a first set of tabs disposed on a first edge of the fluid pump assembly, and ii) a second set of tabs disposed on a second edge of the fluid pump assembly;

the fluid delivery system further comprising: a first ledge and a second ledge, the first ledge disposed on a first side of the cavity, the second ledge disposed on a second side of the cavity;

wherein the multiple retractable loading guides include first loading guides and second loading guides, the first loading guides spaced apart from the second loading guides;

wherein the first loading guides are spaced apart from each other along the first ledge; and wherein the second loading guides are spaced apart from each other along the second ledge.

15. The fluid delivery system as in claim 14, wherein the corresponding channels of the first loading guides align with the first ledge; and wherein the corresponding channels of the second loading guides align with the second ledge.

16. The fluid delivery system as in claim 15, wherein the corresponding channels of the first loading guides are disposed orthogonal with respect to a first direction in which the first loading guides move the fluid pump assembly into the cavity; and wherein the corresponding channels of the second loading guides are disposed orthogonal with respect to the first direction in which the second loading guides move the fluid pump assembly into the cavity.

17. The fluid delivery system as in claim 16, wherein a particular loading guide of the first loading guides includes a stop, the stop disposed in a respective channel of the particular loading guide to retain the fluid pump assembly prior to the multiple retractable loading guides pulling the fluid pump assembly into the cavity, the respective channel of the particular loading guide being one of the corresponding channels of the multiple retractable loading guides.

18. The fluid delivery system as in claim 17, wherein the multiple loading guides are operable to control the movement of the fluid pump assembly in the first direction, which is orthogonal to a second direction in which the tabs are slidably insertable into the respective channels.

* * * * *